US012590134B2

(12) United States Patent
Zhao et al.

(10) Patent No.: US 12,590,134 B2
(45) Date of Patent: Mar. 31, 2026

(54) GLP-1 AGONIST POLYPEPTIDE COMPOUND AND SALT THEREOF, SYNTHESIS METHOD THEREFOR AND USE THEREOF

(71) Applicants: Sinopep-Allsino Biopharmaceutical Co., Ltd., Lianyungang (CN); Hangzhou Sinopep-Allsino Pharmaceutical Technology Development Co., Ltd., Hangzhou (CN)

(72) Inventors: Chengqing Zhao, Lianyungang (CN); Guoqiang Shi, Lianyungang (CN); Shunzi Li, Lianyungang (CN); Caidian Wang, Lianyungang (CN)

(73) Assignees: SINOPEP-ALLSINO BIOPHARMACEUTICAL CO., LTD., Lianyungang (CN); HANGZHOU SINOPEP-ALLSINO PHARMACEUTICAL TECHNOLOGY DEVELOPMENT CO., LTD., Hangzhou (CN)

( * ) Notice: Subject to any disclaimer, the term of this patent is extended or adjusted under 35 U.S.C. 154(b) by 682 days.

(21) Appl. No.: 17/820,251

(22) Filed: Aug. 17, 2022

(65) Prior Publication Data

US 2023/0220033 A1     Jul. 13, 2023

Related U.S. Application Data

(63) Continuation-in-part of application No. PCT/CN2021/076308, filed on Feb. 9, 2021.

(30) Foreign Application Priority Data

Feb. 18, 2020     (CN) .......................... 202010099944.4

(51) Int. Cl.
C07K 14/605     (2006.01)
A61K 38/00      (2006.01)

(52) U.S. Cl.
CPC ............ C07K 14/605 (2013.01); *A61K 38/00* (2013.01)

(58) Field of Classification Search
CPC .... C07K 14/605; C07K 14/001; A61K 38/00; A61P 3/04; A61P 3/10
See application file for complete search history.

(56) References Cited

FOREIGN PATENT DOCUMENTS

| CN | 101133082 A | 2/2008 |
|----|-------------|--------|
| CN | 104356224 A | 2/2015 |
| CN | 101133082 B | 1/2016 |
| CN | 106478806 A | 3/2017 |
| CN | 108034004 A | 5/2018 |
| CN | 111253475 A | 6/2020 |

OTHER PUBLICATIONS

Knudsen, Lotte Bjerre, and Jesper Lau. "The discovery and development of liraglutide and semaglutide." Frontiers in endocrinology 10 (2019): 155. (Year: 2019).*

* cited by examiner

*Primary Examiner* — Lianko G Garyu
*Assistant Examiner* — David Paul Bowles
(74) *Attorney, Agent, or Firm* — MATTHIAS SCHOLL P.C.; Matthias Scholl

(57)                    ABSTRACT

The disclosure provides a GLP-1 agonist polypeptide compound having an amino acid sequence: H $Xaa^1$EGTFTSDVSSYLE $Xaa^2$QAA $Xaa^3$EFIAWLVRGRG (SEQ ID NO: 1). The C-terminal amino acid of the polypeptide compound is a carboxyl or the carboxyl is amidated. $Xaa^1$ and $Xaa^2$ are the same or different; $R_1$ is: a straight-chain or branched-chain alkyl containing 2-6 carbon atoms, $R_2$ is: H or $CH_3$, X is: O, S or N—$CH_3$, in the formula, $R_1$ and R2 alkyl is optionally substituted by 1-6 halogen atoms.

2 Claims, 2 Drawing Sheets

Specification includes a Sequence Listing.

GLP-1 AGONIST POLYPEPTIDE COMPOUND AND SALT THEREOF, SYNTHESIS METHOD THEREFOR AND USE THEREOF

CROSS-REFERENCE TO RELATED APPLICATIONS

This application is a continuation-in-part of International Patent Application No. PCT/CN2021/076308 with an international filing date of Feb. 9, 2021, designating the United States, now pending, and further claims foreign priority benefits to Chinese Patent Application No. 202010099944.4 filed Feb. 18, 2020. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, MA 02142.

BACKGROUND

The disclosure relates to the field of polypeptide compounds, and more particularly to a series of double intestinal insulinotropic peptide analogue compounds, which are a polypeptide compound. The polypeptide compound can activate receptors of human glucagon-like peptide-1 (GLP-1) and can be used for treating type 2 diabetes. The disclosure further relates to a pharmaceutically acceptable salt of the polypeptide compound, a polypeptide pharmaceutical composition, a medicament, a preparation method and an application thereof.

The pathogenesis of metabolic syndrome is abnormal metabolism of various substances such as protein, fat and carbohydrate. Overnutrition and reduced physical activity can lead to obesity and obesity-related diseases such as diabetes. In recent years, the incidence of type 2 diabetes and dyslipidemia has been on the rise; type 2 diabetes is the most common form of diabetes, accounting for about 90% of all diabetes. Type 2 diabetes is characterized by high blood glucose levels caused by insulin resistance. The current standard of care for type 2 diabetes includes diet and exercise and the availability of oral and injectable hypoglycemic agents. Nevertheless, many patients with type 2 diabetes remain inadequately controlled.

GLP-1 is a 37-amino acid peptide that stimulates insulin secretion, protects pancreatic beta cells, and inhibits glucagon secretion, gastric emptying, and food intake, resulting in weight loss. GIP and GLP-1 are known as incretin; Incretin receptor signaling transmission has a physiologically relevant role to maintain glucose homeostasis. In normal physiology, GIP and GLP-1 are secreted from the gut after a meal, and these incretins enhance physiological responses to foods, including satiety, insulin secretion, and nutrient processing. The incretin response is impaired in patients with type 2 diabetes. Currently commercially available incretin analogs or dipeptidyl peptidase IV (DPP-IV) inhibitors utilize a single mechanism of action for glycemic control; if a compound for type 2 diabetes with a dual mechanism of action is used, a polypeptide compound with excellent hypoglycemic activity and weight loss effect can be obtained.

It has been found that the dosage of GLP-1 analogs is limited by side effects such as nausea and vomiting, and therefore administration of a drug often cannot achieve the full efficacy in glycemic control and weight loss. GIP alone has very modest glucose-lowering capacity in patients with type 2 diabetes. Both native GIP and GLP-1 are rapidly inactivated by the ubiquitous protease DPP IV, therefore, they can only be used for short-term metabolic control. DPP IV belongs to the exopeptidase class of proteolytic enzymes; the introduction of unnatural amino acids into the sequence can increase the proteolytic stability of any given peptide, although unnatural amino acids help stabilize the peptide against DPP IV proteolysis and other forms of degradation.

SUMMARY

An object of the disclosure is to provide a series of GLP-1 agonist polypeptide compounds with better hypoglycemic activity and weight loss effect utilizing dual action mechanisms, aiming at the drawbacks of the prior art and in vivo stability, hypoglycemic and weight loss effect and side effects of compounds, etc., so as to treat the diseases of type II diabetes, obesity and cardiovascular diseases, etc.

Another object of the disclosure is to provide a method for preparing the GLP-1 agonist polypeptide compound.

Still another object of the disclosure is to provide a pharmaceutically acceptable salt of the GLP-1 agonist polypeptide compound.

Still another object of the disclosure is to provide a pharmaceutical composition of the GLP-1 agonist polypeptide compound.

Still another object of the disclosure is to provide a medicament of the GLP-1 agonist polypeptide compound.

Still another object of the disclosure is to provide the GLP-1 agonist polypeptide compound, a pharmaceutically acceptable salt thereof, a pharmaceutical composition thereof and an application of a medicament.

The object of the disclosure is achieved with the following technical solution. The disclosure discloses a GLP-1 agonist polypeptide compound. The GLP-1 agonist polypeptide compound is characterized in that the amino acid sequence of the polypeptide compound is:

H Xaa$^1$EGTFTSDVSSYLE Xaa$^2$QAA Xaa$^3$EFIAWLVRGRG (SEQ ID NO: 1), wherein the C-terminal amino acid of the polypeptide compound is carboxyl or amidated as carboxyl;

wherein:

Xaa$^1$ is:

Xaa$^2$ is: G,

-continued

Xaa$^1$ and Xaa$^2$ are the same or different;

R$_1$ is: a straight-chain or branched-chain alkyl containing 2-6 carbon atoms,

R$_2$ is: H or CH$_3$,

X is: O, S or N—CH$_3$, in the formula, R$_1$ and R$_2$ alkyl is optionally substituted by 1-6 halogen atoms;

Xaa$^3$ is:

in the above formula, m and n are natural numbers, preferably, n is a natural number ranging from 12 to 20; and preferably, m is a natural number ranging from 0 to 3.

A further preferred technical solution of the GLP-1 agonist polypeptide compound of the disclosure is that the amino acid sequence of the polypeptide compound is preferably shown as follows:

(1)
NO: 1
HX$_2$EGTFTSDVSSYLEX$_2$QAAK(HOOC-(CH$_2$)$_{16}$-CO-γ-Glu-AEEA-AEEA)EFIAWLVRGRG (2)
NO: 2
HX$_2$EGTFTSDVSSYLEX$_1$QAAK(HOOC-(CH$_2$)$_{16}$-CO-γ-Glu-AEEA-AEEA)EFIAWLVRGRG (3)
NO: 3
HX$_3$EGTFTSDVSSYLEX$_3$QAAK(HOOC-(CH$_2$)$_{16}$-CO-γ-Glu-AEEA-AEEA)EFIAWLVRGRG (4)
NO: 4
HX$_3$EGTFTSDVSSYLEX$_1$QAAK(HOOC-(CH$_2$)$_{16}$-CO-γ-Glu-AEEA-AEEA)EFIAWLVRGRG (5)
NO: 5
HX$_4$EGTFTSDVSSYLEX$_4$QAAK(HOOC-(CH$_2$)$_{16}$-CO-γ-Glu-AEEA-AEEA)EFIAWLVRGRG (6)
NO: 6
HX$_4$EGTFTSDVSSYLEX$_1$QAAK(HOOC-(CH$_2$)$_{16}$-CO-γ-Glu-AEEA-AEEA)EFIAWLVRGRG (7)
NO: 7
HX$_5$EGTFTSDVSSYLEX$_5$QAAK(HOOC-(CH$_2$)$_{16}$-CO-γ-Glu-AEEA-AEEA)EFIAWLVRGRG

-continued (8)
NO: 8
HX$_5$EGTFTSDVSSYLEX$_1$QAAK(HOOC-(CH$_2$)$_{16}$-CO-γ-Glu-AEEA-AEEA)EFIAWLVRGRG (9)
NO: 9
HX$_6$EGTFTSDVSSYLEX$_6$QAAK(HOOC-(CH$_2$)$_{16}$-CO-γ-Glu-AEEA-AEEA)EFIAWLVRGRG

(10)
NO: 10
HX$_6$EGTFTSDVSSYLEX$_1$QAAK(HOOC-(CH$_2$)$_{16}$-CO-γ-Glu-AEEA-AEEA)EFIAWLVRGRG

-continued

(11)
NO: 11
HX$_7$EGTFTSDVSSYLEX$_7$QAAK(HOOC-(CH$_2$)$_{16}$-CO-γ-Glu-AEEA-AEEA)EFIAWLVRGRG

(12)
NO: 12
HX$_7$EGTFTSDVSSYLEX$_1$QAAK(HOOC-(CH$_2$)$_{16}$-CO-γ-Glu-AEEA-AEEA)EFIAWLVRGRG

(13)
NO: 13
HX$_8$EGTFTSDVSSYLEX$_8$QAAK(HOOC-(CH$_2$)$_{16}$-CO-γ-Glu-AEEA-AEEA)EFIAWLVRGRG

(14)
NO: 14
HX$_8$EGTFTSDVSSYLEX$_1$QAAK(HOOC-(CH$_2$)$_{16}$-CO-γ-Glu-AEEA-AEEA)EFIAWLVRGRG

(15)
NO: 15
HX$_9$EGTFTSDVSSYLEX$_9$QAAK(HOOC-(CH$_2$)$_{16}$-CO-γ-Glu-AEEA-AEEA)EFIAWLVRGRG

(16)
NO: 16
HX$_9$EGTFTSDVSSYLEX$_1$QAAK(HOOC-(CH$_2$)$_{16}$-CO-γ-Glu-AEEA-AEEA)EFIAWLVRGRG

(17)
NO: 17
HX$_{10}$EGTFTSDVSSYLEX$_{10}$QAAK(HOOC-(CH$_2$)$_{16}$-CO-γ-Glu-AEEA-AEEA)EFIAWLVRGRG

(18)
NO: 18
HX$_{10}$EGTFTSDVSSYLEX$_1$QAAK(HOOC-(CH$_2$)$_{16}$-CO-γ-Glu-AEEA-AEEA)EFIAWLVRGRG

(19)
NO: 19
HX$_{11}$EGTFTSDVSSYLEX$_{11}$QAAK(HOOC-(CH$_2$)$_{16}$-CO-γ-Glu-AEEA-AEEA)EFIAWLVRGRG

(20)
NO: 20
HX$_{11}$EGTFTSDVSSYLEX$_1$QAAK(HOOC-(CH$_2$)$_{16}$-CO-γ-Glu-AEEA-AEEA)EFIAWLVRGRG

-continued (21)

NO: 21

HX$_{12}$EGTFTSDVSSYLEX$_{12}$QAAK(HOOC-(CH$_2$)$_{16}$-CO-γ-Glu-AEEA-AEEA)EFIAWLVRGRG (22)

NO: 22

HX$_{12}$EGTFTSDVSSYLEX$_1$QAAK(HOOC-(CH$_2$)$_{16}$-CO-γ-Glu-AEEA-AEEA)EFIAWLVRGRG

Wherein:

$X_1$ = G; $X_2$ = ; $X_3$ = ;

$X_4$ = ; $X_5$ = ;

$X_6$ = ; $X_7$ = ;

$X_8$ = ; $X_9$ = ;

$X_{10}$ = ; $X_{11}$ = ;

-continued $X_{12}$ =

The disclosure further discloses a method for synthesizing the GLP-1 agonist polypeptide compound. The method is characterized in that (1) The 1$^{st}$ to 4$^{th}$ amino acids of the 1st to 31$^{st}$ amino acids of a main sequence of a solid-phase synthesis compound polypeptide adopt a fragment Boc-His(Trt)-Xaa$^1$-Glu(OtBu)-Gly-OH, wherein:

Xaa$^1$ is:

R1 is: a straight-chain or branched-chain alkyl containing 2-6 carbon atoms, $R_2$ is: H or CH$_3$, X is: O, S or N—CH$_3$, in the formula, $R_1$ and $R_2$alkyl is optionally substituted by 1-6 halogen atoms;

(2) The Lys at position 20 adopts a fragment Fmoc-Lys (Xaa$^3$); the structural formula of the fragment is as follows:

n is a natural number ranging from 12 to 20; and m is a natural number ranging from 0 to 3;

(3) A condensing agent used is one or more of DIC/HOBt, DIC/Oxymapure, HBTU/HOBt/DIEA, PyBop/HOBt/DIEA; a reaction solvent used is one or a combination of more of DCM, DMF, NMP and DMSO; and an Fmoc removal agent used is a v/v 25% piperidine/DMF solution;

(4) The method comprises the following steps:

Step 1, preparing Fmoc-Gly$^{31}$-Wang resin;

Step 2, preparing fully-protected peptide resin;

Step a, adding the Fmoc-Gly$^{31}$-Wang resin to a solid-phase reactor;

Step b, coupling Fmoc-Arg$^{30}$(Pbf)-OH, Fmoc-Gly$^{29}$-OH, Fmoc-Arg$^{28}$(Pbf)-OH, Fmoc-Val$^{27}$-OH, Fmoc-Leu$^{26}$-OH, Fmoc-Trp$^{25}$(Boc)-OH, Fmoc-Ala$^{24}$-OH, Fmoc-Ile$^{23}$-OH, Fmoc-Phe$^{22}$-OH, Fmoc-Glu$^{21}$(OtBu)-OH, Fmoc-Lys$^{20}$(Xaa$^3$)-OH, Fmoc-Ala$^{19}$-OH, Fmoc-Ala$^{18}$-OH, Fmoc-Gln$^{17}$(Trt)-OH, Fmoc-Gly$^{16}$-OH, Fmoc-Glu$^{15}$(OtBu)-OH, Fmoc-Leu$^{14}$-OH, Fmoc-Tyr$^{13}$(tBu)-OH, Fmoc-Ser$^{12}$(tBu)-OH, Fmoc-Ser$^{11}$(tBu)-OH, Fmoc-Val$^{10}$-OH, Fmoc-Asp$^9$(OtBu)-OH, Fmoc-Ser$^8$(tBu)-OH, Fmoc-Thr$^7$(tBu)-OH, Fmoc-Phe$^6$-OH, Fmoc-Thr$^5$(tBu)-OH, Boc-His$^1$(Trt)-Xaa$^1$-Glu$^3$(OtBu)-Gly$^4$-OH to Fmoc-Gly$^{31}$-Wang one by one by using a solid-phase synthesis method;

Xaa$^1$ is:

R$_1$ is: a straight-chain or branched-chain alkyl containing 2-6 carbon atoms,

R$_2$ is: H or CH$_3$,

X is: O, S or N—CH$_3$, in the formula, R$_1$ and R$_2$ alkyl is optionally substituted by 1-6 halogen atoms;

The fragment Fmoc-Lys$^{20}$(Xaa$^3$)-OH has a structural formula as follows:

n is a natural number ranging from 12 to 20; and m is a natural number ranging from 0 to 3.

Step 3, cracking the peptide resin to obtain a crude peptide, wherein a cracking agent is a composite agent with a ratio of TFA: (thioanisole/TIS/EDT/phenol/water)=95:5, wherein a capturing agent is any combination of thioanisole/TIS/EDT/phenol/water.

Step 4, preparing a polypeptide compound by a reversed phase chromatography, wherein reversed phase chromatography fillers are silica-gel bonded C8 and C18 fillers, and a mobile phase adopts acetonitrile and an aqueous solution, and the aqueous solution is TFA, phosphoric acid and a sulfuric acid solution at a certain pH, or a sodium salt, a potassium salt, an ammonium salt, etc. generated by these acids.

The disclosure also discloses a pharmaceutically acceptable salt of the GLP-1 agonist polypeptide compound. The GLP-1 agonist polypeptide compound is the polypeptide compound as described in the technical solution, and the C-terminal amino acid of the polypeptide compound is amidated as C-terminal primary amide or the pharmaceutically acceptable salt thereof is amidated.

For the pharmaceutically acceptable salt of the GLP-1 agonist polypeptide compound of the disclosure, the preferred technical solution is: the salt is a salt formed by the GLP-1 agonist polypeptide compound and one of the following compounds: hydrochloric acid, hydrobromic acid, hydroiodic acid, sulfuric acid, pyrosulfuric acid, phosphoric acid, nitric acid, methanesulfonic acid, ethanesulfonic acid, benzenesulfonic acid, p-toluenesulfonic acid, formic acid, acetic acid, acetoacetic acid, pyruvic acid, trifluoroacetic acid, propionic acid, butyric acid, caproic acid, heptanoic acid, undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, niacin, pamoic acid, pectinic acid, persulfuric acid, 3-phenylpropionic acid, picric acid, pivalic acid, 2-hydroxyethanesulfonic acid, itaconic acid, sulfamic acid, trifluoromethanesulfonic acid, dodecyl sulfuric acid, 2-naphthalene sulfonic acid, naphthalenedisulfonic acid, camphor sulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptanoic acid, glycerophosphoric acid, aspartic acid, sulfosalicylic acid, hemisulfuric acid or thiocyanic acid.

The disclosure also discloses a pharmaceutical composition of the GLP-1 agonist polypeptide compound. The pharmaceutical composition is characterized by being prepared by taking the GLP-1 agonist polypeptide compound described in any one of the above technical solutions as an effective raw material or taking a pharmaceutically acceptable salt of any one GLP-1 agonist polypeptide compound in the technical solution as an effective raw material and adding a pharmaceutically acceptable carrier or diluent.

The pharmaceutically acceptable salt of the GLP-1 agonist polypeptide compound is prepared by taking the GLP-1 agonist polypeptide compound and the above compound as raw materials and adopting a conventional method disclosed in the prior art.

The disclosure also discloses a medicament prepared from the GLP-1 agonist polypeptide compound described in any one of the above technical solutions. The medicament is any one of a tablet, a capsule, an elixir, syrup, a lozenge, an inhalant, a spray, an injection, a film, a patch, powder, a granule, a block, an emulsion, a suppository or a compound preparation in pharmacy, and the medicament is prepared from the GLP-1 agonist polypeptide compound and a pharmaceutically acceptable pharmaceutic adjuvant, carrier or diluent. The medicament can be prepared according to a conventional method in the prior art.

According to the application of the GLP-1 agonist polypeptide compound in the disclosure, the GLP-1 agonist polypeptide compound can be used as an effective raw material for preparing a medicine for treating or preventing diabetes mellitus or preparing a weight-losing medicine.

According to the pharmaceutical application of the GLP-1 agonist polypeptide compound in the disclosure, the GLP-1 agonist polypeptide compound can be used as an effective raw material for preparing a medicine for treating or preventing diabetes mellitus or preparing a weight-losing medicine.

The pharmaceutical composition and the medicament of the GLP-1 agonist polypeptide compound in the disclosure can be used as a medicine for treating and preventing diabetes mellitus or a weight-losing medicine.

In this specification, the meanings of the following abbreviations are shown in the table below:

| Abbreviation | Meaning |
| --- | --- |
| DCM | Dichloromethane |
| DMF | N,N-Dimethylformamide |
| HBTU | Benzotriazole-N,N,N',N'-tetramethylurea hexafluorophosphate |
| HOBt | 1-hydroxy-benzotriazole |
| DIEA/DIPEA | N,N'-diisopropylethylamine |
| Fmoc | N-9-fluorenemethoxycarbonyl |
| EDT | Ethanedithiol |
| HPLC | High performance liquid chromatography |
| TFA | Trifluoroacetate |
| tBu | Tert-butyl |

As a part of the disclosure, substitution of non-natural amino acid not only has a greater effect on improvement of in-vivo stability of a GLP-1 agonist, but also has a greater effect on activity. For example, when different amino acids $Xaa^1$ are used in the sequence, the activity of the GLP-1 agonist changes greatly, and when $Xaa^1$ has chirality, one of optical isomers has higher activity than that of another substituted GLP-1 agonist. Besides, fatty acid can improve pharmacokinetics of peptide by prolonging half-life with an albumin binding sequence motif. Although the half-life of the peptide can be improved by the fatty acid, the applicant finds that as a part of the disclosure, the length, the composition and the position of a fatty acid chain and a connector between the peptide and the fatty acid chain possibly have unexpected effects on the activity of the GLP-1 agonist, and meanwhile, the half-life of the peptide is prolonged.

Compared with the prior art, the disclosure has the following beneficial effects:

The disclosure discloses a series of GLP-1 agonist polypeptide compounds with better hypoglycemic activity and weight loss effect utilizing dual action mechanisms; in addition, the polypeptide compounds have the cardiovascular benefits, and can be used as the effective raw material for preparing the medicine for treating or preventing diabetes or the weight-losing medicines. Based on animal energy consumption data, the polypeptide compounds have the effect of losing weight of patients, have low immunogenic properties and a pharmacokinetic (PK) profile supporting once-weekly dosing, and are suitable for serving as active ingredients of a medicine for treating diabetes and obesity; thus, the polypeptide compounds can be used for treatment of type 2 diabetes, obesity and cardiovascular diseases, etc.

The GLP-1 agonist polypeptide compound prepared by the method has good activity of reducing blood glucose and slowing weight gain, and is long in effect time, high in yield, short in synthesis period, easy in crude product purification, low in production cost and easy for automatic industrial production.

DETAILED DESCRIPTION

Figure 1:
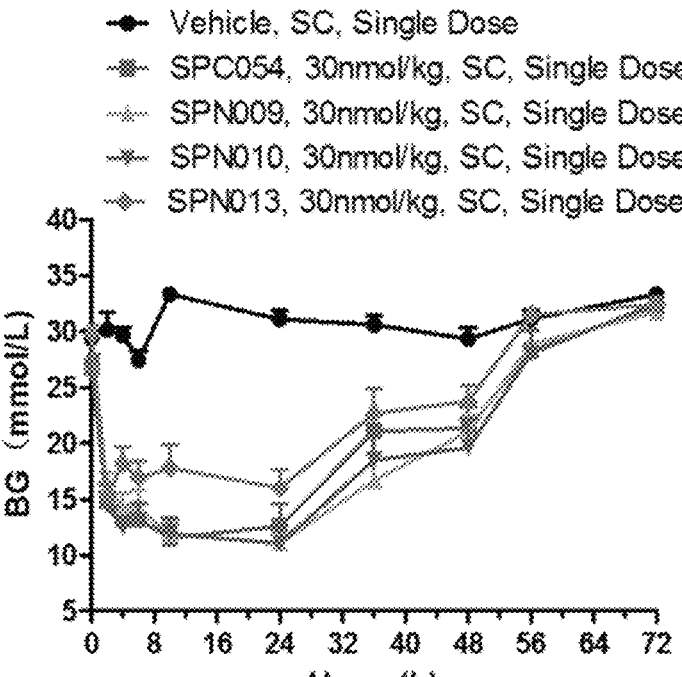
FIG. 1 is a diagram showing the effect of each test drug on the random blood sugar of db/db mice in the experiment.

The disclosure is described with the following embodiments, but these embodiments do not constitute any limitation to the rights of the disclosure.

In the formula:

-continued $X_8 =$ $X_9 =$ $X_{10} =$ $X_{11} =$ $X_{12} =$

Example 1

Synthesis of Polypeptide Compound of NO: 1:

HX₂EGTFTSDVSSYLEX₂QAAK(HOOC-(CH₂)₁₆-CO-γ-Glu-AEEA-AEEA)EFIAWLVRGRG

1.1 Swelling of Resin 10 g of Wang-Resin (with the substitution degree of 0.53 mmol/g) was weighed and swelled for 30 min with 100 mL of DCM, suction filtration was conducted to remove DCM, swelling was conducted for 30 min with 100 mL of DMF, and the resin was washed with 100 mL of DMF and 100 mL of DCM respectively.

1.2 Synthesis of Fmoc-Gly-Wang-Resin

Fmoc-Gly-OH (15 mmol), HOBt (18 mmol) and DIC (18 mmol) were dissolved in 100 mL of DMF, then the solution was added into resin obtained in the previous step to react for 2 hours, after reaction ended, the reaction solution was filtered out, and the resin was washed 3 times with 100 mL of DCM and 100 mL of DMF respectively.

1.3 Removal of Fmoc Protecting Group

A 25% piperidine/DMF (V/V) solution containing 0.1 M of HOBt was added into the washed resin to remove Fmoc, and after the reaction ended, the resin was washed 3 times with 100 mL of DCM and 100 mL of DMF respectively.

1.4 Extension of Peptide Chain

According to the sequence, the steps of deprotection and coupling were repeated to sequentially bind corresponding amino acids, and the corresponding amino acids were sequentially bound until peptide chain synthesis was completed, to obtain the peptide resin. The specific coupling protected amino acids were as follows:

Fmoc-Arg³⁰(Pbf)-OH, Fmoc-Gly²⁹-OH, Fmoc-Arg²⁸ (Pbf)-OH, Fmoc-Val²⁷-OH, Fmoc-Leu²⁶-OH, Fmoc-Trp²⁵ (Boc)-OH, Fmoc-Ala²⁴-OH, Fmoc-Ile²³-OH, Fmoc-Phe²²-OH, Fmoc-Glu²¹(OtBu)-OH, Fmoc-Lys²⁰(Xaa³)-OH, Fmoc-Ala¹⁹-OH, Fmoc-Ala¹⁸-OH, Fmoc-Gln¹⁷(Trt)-OH, Fmoc-X₂-OH, Fmoc-Glu¹⁵(OtBu)-OH, Fmoc-Leu¹⁴-OH, Fmoc-Tyr¹³(tBu)-OH, Fmoc-Ser¹²(tBu)-OH, Fmoc-Ser¹¹ (tBu)-OH, Fmoc-Val¹⁰-OH, Fmoc-Asp⁹(OtBu)-OH, Fmoc-Ser⁸(tBu)-OH, Fmoc-Thr⁷(tBu)-OH, Fmoc-Phe⁶-OH, Fmoc-Thr⁵(tBu)-OH, Boc-His¹(Trt)-X₂-Glu³(OtBu)-Gly⁴-

OH were coupled to Fmoc-Gly³¹-Wang one by one by using a solid-phase synthesis method;

1.5 Cleavage of Peptide Resin

Trifluoroacetic acid was measured to a reactor and cooled to −10° C. to 0° C., triisopropylsilane, 1,2-dithioglycol and purified water (TFA:TIS:EDT:H₂O=95:2:2:1) were added and stirred to be uniformly mixed. Peptide resin was slowly added, heated to 20-30° C., and a cracking reaction was conducted for 115-125 min. After the reaction ended, the resin was filtered out, the filtered resin was washed with M×8×20% ml of TFA, the filtered solution and the washing solution were completely transferred into M×8×1.2×4 ml of diethyl ether, stirred for 5-10 min, kept standing to precipitate for 15 min or more. The precipitated turbid liquid was added into a centrifugal machine, and solids were centrifuged and collected; the solids were washed with diethyl ether six times, and the amount of diethyl ether used each time was not less than 5 L. The solids were subjected to vacuum drying for 6-10 hat the temperature of 20-35° C., and 10.90 g of crude peptide was obtained.

2. Purification of NO: 1 Polypeptide Compound

Purification was conducted through preparative liquid chromatography, and the chromatographic conditions were that a C18 column (100 mm×250 mm, 10 μm) was adopted; a mobile phase A was 0.1% H₃PO₄/water (V/V), and a mobile phase B was 0.1% H₃PO₄/acetonitrile (V/V); the mobile phase gradient was 20%-60% of the mobile phase B, and the time was 60 min; the flow velocity was 200 mL/min, the detection wavelength was 214 nm, fractions with the purity larger than 98.0% were collected, and 3.10 g of samples were obtained through freeze drying after rotary evaporation and concentration.

The synthesis methods of polypeptide compounds of NO: 2-30 were the same as that of Example 1:

Example 2

Synthesis of Polypeptide Compound of NO: 2:

HX₂EGTFTSDVSSYLEX₁QAAK(HOOC-(CH₂)₁₆-CO-γ-Glu-AEEA-AEEA)EFIAWLVRGRG

The synthesis procedures were the same as those in Example, and the purified sample solution was collected and freeze-dried to obtain a purified product in a mass of 3.93 g.

Example 3

Synthesis of Polypeptide Compound of NO: 3:

HX₃EGTFTSDVSSYLEX₃QAAK(HOOC-(CH₂)₁₆-CO-γ-Glu-AEEA-AEEA)EFIAWLVRGRG

The synthesis procedures were the same as those in Example, and the purified sample solution was collected and freeze-dried to obtain a purified product in a mass of 2.87 g.

Example 4

Synthesis of Polypeptide Compound of NO: 4:

HX₃EGTFTSDVSSYLEX₁QAAK(HOOC-(CH₂)₁₆-CO-γ-Glu-AEEA-AEEA)EFIAWLVRGRG

The synthesis procedures were the same as those in Example, and the purified sample solution was collected and freeze-dried to obtain a purified product in a mass of 2.55 g.

Example 5

Synthesis of Polypeptide Compound of NO: 5

HX$_4$EGTFTSDVSSYLEX$_4$QAAK(HOOC-(CH$_2$)$_{16}$-CO-γ-Glu-AEEA-AEEA)EFIAWLVRGRG

The synthesis procedures were the same as those in Example, and the purified sample solution was collected and freeze-dried to obtain a purified product in a mass of 2.60 g.

Example 6

Synthesis of Polypeptide Compound of NO: 6

HX$_4$EGTFTSDVSSYLEX$_1$QAAK(HOOC-(CH$_2$)$_{16}$-CO-γ-Glu-AEEA-AEEA)EFIAWLVRGRG

The synthesis procedures were the same as those in Example, and the purified sample solution was collected and freeze-dried to obtain a purified product in a mass of 2.61 g.

Example 7

Synthesis of Polypeptide Compound of NO: 7

HX$_5$EGTFTSDVSSYLEX$_5$QAAK(HOOC-(CH$_2$)$_{16}$-CO-γ-Glu-AEEA-AEEA)EFIAWLVRGRG

The synthesis procedures were the same as those in Example, and the purified sample solution was collected and freeze-dried to obtain a purified product in a mass of 3.1 g.

Example 8

Synthesis of Polypeptide Compound of NO: 8

HX$_5$EGTFTSDVSSYLEX$_1$QAAK(HOOC-(CH$_2$)$_{16}$-CO-γ-Glu-AEEA-AEEA)EFIAWLVRGRG

The synthesis procedures were the same as those in Example, and the purified sample solution was collected and freeze-dried to obtain a purified product in a mass of 3.35 g.

Example 9

Synthesis of Polypeptide Compound of NO: 9

HX$_6$EGTFTSDVSSYLEX$_6$QAAK(HOOC-(CH$_2$)$_{16}$-CO-γ-Glu-AEEA-AEEA)EFIAWLVRGRG

The synthesis procedures were the same as those in Example, and the purified sample solution was collected and freeze-dried to obtain a purified product in a mass of 2.70 g.

Example 10

Synthesis of Polypeptide Compound of NO: 10

HX$_6$EGTFTSDVSSYLEX$_1$QAAK(HOOC-(CH$_2$)$_{16}$-CO-γ-Glu-AEEA-AEEQ)-EFIAWLVRGRG

The synthesis procedures were the same as those in Example, and the purified sample solution was collected and freeze-dried to obtain a purified product in a mass of 3.90 g.

Example 11

Synthesis of Polypeptide Compound of NO: 11

HX$_7$EGTFTSDVSSYLEX$_7$QAAK(HOOC-(CH$_2$)$_{16}$-CO-γ-Glu-AEEA-AEEA)EFIAWLVRGRG

The synthesis procedures were the same as those in Example, and the purified sample solution was collected and freeze-dried to obtain a purified product in a mass of 3.74 g.

Example 12

Synthesis of Polypeptide Compound of NO: 12

HX$_7$EGTFTSDVSSYLEX$_7$QAAK(HOOC-(CH$_2$)$_{16}$-CO-γ-Glu-AEEA-AEEA)EFIAWLVRGRG

The synthesis procedures were the same as those in Example, and the purified sample solution was collected and freeze-dried to obtain a purified product in a mass of 3.22 g.

Example 13

Synthesis of Polypeptide Compound of NO: 13

HX$_8$EGTFTSDVSSYLEX$_8$QAAK(HOOC-(CH$_2$)$_{16}$-CO-γ-Glu-AEEA-AEEA)EFIAWLVRGRG

The synthesis procedures were the same as those in Example, and the purified sample solution was collected and freeze-dried to obtain a purified product in a mass of 3.48 g.

Example 14

Synthesis of Polypeptide Compound of NO: 14

HX$_8$EGTFTSDVSSYLEX$_8$QAAK(HOOC-(CH$_2$)$_{16}$-CO-γ-Glu-AEEA-AEEA)EFIAWLVRGRG

The synthesis procedures were the same as those in Example, and the purified sample solution was collected and freeze-dried to obtain a purified product in a mass of 5.30 g.

Example 15

Synthesis of Polypeptide Compound of NO: 15

HX$_9$EGTFTSDVSSYLEX$_9$QAAK(HOOC-(CH$_2$)$_{16}$-CO-γ-Glu-AEEA-AEEA)EFIAWLVRGRG

The synthesis procedures were the same as those in Example, and the purified sample solution was collected and freeze-dried to obtain a purified product in a mass of 2.70 g.

Example 16

Synthesis of Polypeptide Compound of NO: 16

HX$_9$EGTFTSDVSSYLEX$_1$QAAK(HOOC-(CH$_2$)$_{16}$-CO-γ-Glu-AEEA-AEEA)EFIAWLVRGRG

The synthesis procedures were the same as those in Example, and the purified sample solution was collected and freeze-dried to obtain a purified product in a mass of 3.67 g.

Example 17

Synthesis of Polypeptide Compound of NO: 17

$HX_{10}EGTFTSDVSSYLEX_{10}QAAK(HOOC-(CH_2)_{16}-CO-\gamma-Glu-AEEA-AEEA)EFIAWLVRGRG$ The synthesis procedures were the same as those in Example, and the purified sample solution was collected and freeze-dried to obtain a purified product in a mass of 2.33 g.

Example 18

Synthesis of Polypeptide Compound of NO: 18

$HX_{10}EGTFTSDVSSYLEX_1QAAK(HOOC-(CH_2)_{16}-CO-\gamma-Glu-AEEA-AEEA)EFIAWLVRGRG$ The synthesis procedures were the same as those in Example, and the purified sample solution was collected and freeze-dried to obtain a purified product in a mass of 3.440 g.

Example 19

Synthesis of Polypeptide Compound of NO: 19

$HX_{11}EGTFTSDVSSYLEX_{11}QAAK(HOOC-(CH_2)_{16}-CO-\gamma-Glu-AEEA-AEEA)EFIAWLVRGRG$ The synthesis procedures were the same as those in Example, and the purified sample solution was collected and freeze-dried to obtain a purified product in a mass of 2.70 g.

Example 20

Synthesis of Polypeptide Compound of NO: 20

$HX_{11}EGTFTSDVSSYLEX_1QAAK(HOOC-(CH_2)_{16}-CO-\gamma-Glu-AEEA-AEEA)EFIAWLVRGRG$ The synthesis procedures were the same as those in Example, and the purified sample solution was collected and freeze-dried to obtain a purified product in a mass of 3.92 g.

Example 21

Synthesis of Polypeptide Compound of NO: 21

$HX_{12}EGTFTSDVSSYLEX_{12}QAAK(HOOC-(CH_2)_{16}-CO-\gamma-Glu-AEEA-AEEA)EFIAWLVRGRG$ The synthesis procedures were the same as those in Example, and the purified sample solution was collected and freeze-dried to obtain a purified product in a mass of 3.62 g.

Example 22

Synthesis of Polypeptide Compound of NO: 22

$HX_{12}EGTFTSDVSSYLEXQAAK(HOOC-(CH_2)_{16}-CO-\gamma-Glu-AEEA-AEEA)EFIAWLVRGRG$ The synthesis procedures were the same as those in Example, and the purified sample solution was collected and freeze-dried to obtain a purified product in a mass of 3.80 g.

The relevant pharmacological experimental methods and results of a GLP-1 agonist polypeptide compound (hereinafter referred to as a polypeptide compound):

1. GLP-1 Receptor Agonist Activity of Polypeptide Compound

A glucagon-like peptide-1 receptor (GLP-1R) belongs to a B-type G protein coupling receptor, and plays an important role in the conditions of blood glucose and weight and is recognized as an important target of antidiabetic drugs. A Chinese hamster ovary cell line (CHO) capable of stably expressing human GLP-1R was used for measuring the induction activity of a polypeptide compound sample and a control compound to a GLP-1R downstream cAMP signal.

A wild human GLP-1R (NM_002062.5) was subjected to transient transfection and screened for two weeks by 600 μg/ml of hygromycin-B to obtain a cell line which was recombined and integrated into an FlpInCHO (Invitrogen) cell stable expression system. The culture condition of the FlpInCHO cell was as follows: 10% of heat-inactivated fetal calf serum was added to a DMEM culture solution, and the culture was performed in a 5% carbon dioxide cell incubator.

In a downstream cAMP signal detection test, cells were placed in a 6-well cell culture plate for overnight culture, then transferred into a 384-well plate according to the concentration of 8,000 cells in each well and continuously cultured for 24 h under the conditions of 37° C. and 5% of $CO_2$. In the test, an LANCE cAMP detection kit was used for measuring the cAMP signal intensity. After the cells were incubated for 30 min, the LANCE cAMP detection kit was used, a microplate reader was used for measuring fluorescence value, a standard curve was established to convert the fluorescence value into corresponding cAMP value, and the $EC_{50}$ value of the compound was calculated by nonlinear regression of Graphpad Prism 7.0 software.

cAMP Signal Analysis of GLP-1R

| Peptides | GLP-1R $EC_{50}$ (pM) |
|---|---|
| Semaglutide | 645.17 ± 48.37 |
| GLP-1(7-36) | 121.64 ± 87.78 |
| NO: 1 | 91733.33 ± 9692.46 |
| NO: 2 | 21410.0 ± 1320.27 |
| NO: 3 | 2842.33 ± 512.87 |
| NO: 4 | 2024.33 ± 276.5 |
| NO: 5 | 914.63 ± 126.1 |
| NO: 6 | 623.22 ± 83.5 |
| NO: 7 | 8795.33 ± 1407 |
| NO: 8 | 7924.72 ± 1062 |
| NO: 9 | 675.33 ± 67 |
| NO: 10 | 524.72 ± 52 |
| NO: 11 | 8095.65 ± 507 |
| NO: 12 | 8924.22 ± 310 |
| NO: 13 | 5590.19 ± 575 |
| NO: 14 | 5400.39 ± 364.7 |
| NO: 15 | 2901.56 ± 390 |
| NO: 16 | 2508.81 ± 307 |
| NO: 17 | 3324.82 ± 677.2 |
| NO: 18 | 3124.17 ± 511.8 |
| NO: 19 | 791.33 ± 63.5 |
| NO: 20 | 692.89 ± 55.7 |
| NO: 21 | 652.07 ± 41.7 |
| NO: 22 | 630.43 ± 51.9 |

An in-vivo animal test was carried out for polypeptide compounds NO: 3 and NO: 4, a detailed comparison experiment was carried out in the aspects of hypoglycemic effect and weight loss, and the experiment scheme and results were as follows.

Experiments on Glucose Lowering of Polypeptide Compound and Effect on Weight

After DB/DB mice with high blood glucose were acclimated for 5-7 days, a non-fasting random blood glucose level was determined; after fasting for 12 h, a fasting blood glucose level was determined by a rapid blood glucose meter. With comprehensive consideration on the body weight, and fasting blood glucose 12 hours after fasting and random blood glucose results, the animals were randomly grouped (random block design) and were divided into a solvent control group, a polypeptide compound group (selected test drugs: NO: 3 and NO: 4), a positive control Semaglutide group and a known control group SPN013 according to the random weight, the random blood glucose and the fasting blood glucose. Mice in each test drug group and each control group received single subcutaneous injection of each test drug or a control solution respectively, and the mice in the model control group received single subcutaneous injection of PBS buffer solution; and the experiment grouping and dosage setting conditions were shown in Table 1:

TABLE 1

Grouping of experimental animals before administration

| Group | Dose (nmol/kg) | Volume parameter of administration (μL/g) | Route of administration | Frequency of administration | n |
|---|---|---|---|---|---|
| Solvent control (PBS) | — | 5 | SC | Single dose | 8 |
| Semaglutide | 30 | 5 | SC | Single dose | 8 |
| NO: 3 | 30 | 5 | SC | Single dose | 8 |
| NO: 4 | 30 | 5 | SC | Single dose | 8 |
| SPNO13 | 30 | 5 | SC | Single dose | 8 |

Note: n: the number of the mice in each group; dosing volume: 5 μl/g according to the body weight of the mice.

Experimental instrument: fast blood glucose meter (Johnson & Johnson, One Touch UltraEasy; instrument serial number: MGC23B4ER, MGC23B5ER)

Experimental Observation:

Clinical symptoms: the formulation of this experimental protocol and any modification would be implemented after evaluation and approval by the Institutional Animal Care and Use Committee (IACUC) of the Shanghai Institute of Materia Medica. Animal health and death were monitored daily.

Body weight: after grouping the animals, the body weight was measured once a day at a fixed time period Experimental Indicators:

Blood glucose level: the blood was taken from the tail tip of the mice to measure the blood glucose level with a fast blood glucose meter and blood glucose test strips.

After grouping, different test articles were subcutaneously administered once, and blood glucose levels were measured in 0 h, 2 h, 4 h, 6 h, 10 h, 24 h, 34 h, 48 h, 58 h, 72 h, 82 h, and 96 h following the administration, respectively.

The glucose lowering effect of the test article was evaluated by BG (mmol/L) or AUC (mmol/L·min).

Calculation of AUC:

$$AUC=[(BG_0+BG_2)\times2+(BG_2+BG_4)\times2+(BG_4+BG_6)\times2+$$
$$(BG_6+BG_{10})\times4+(BG_{10}+BG_{24})\times14+(BG_{24}+$$
$$BG_{34})\times10+(BG_{34}+BG_{48})\times14+(BG_{48}+BG_{58})\times10+$$
$$(BG_{58}+BG_{72})\times14+(BG_{72}+BG_{82})\times10+(BG_{82}+$$
$$BG_{96})\times14]/2.$$

Data Analysis:

T test was used for comparison between two groups. One-way ANOVA was used for comparison among three or more groups. If there was a significant difference in F value, multiple comparisons should be performed after ANOVA analysis. All data analyses were performed with SPSS 17.0. If $p<0.05$, it was considered a significant difference.

Figure 2:
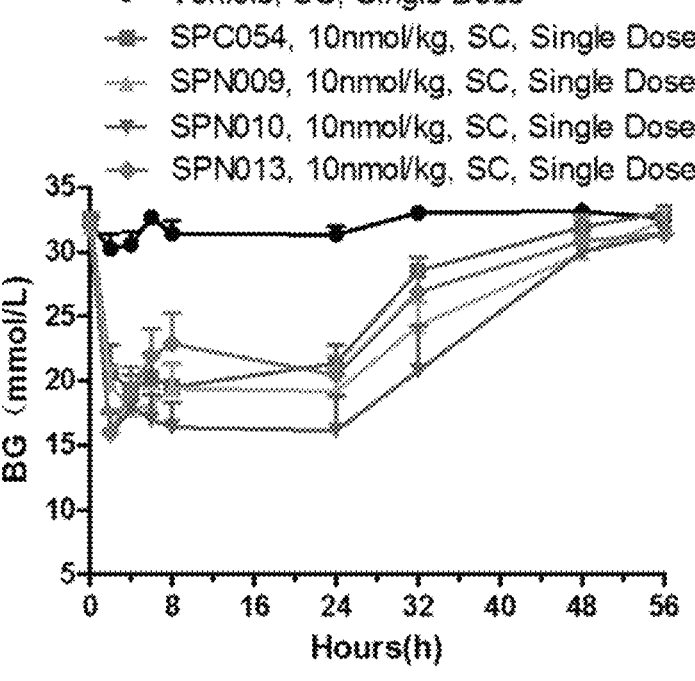
FIG. 2 is a diagram showing the rate of change of each test drug to random blood sugar in db/db mice in the experiment.
Figure 3:
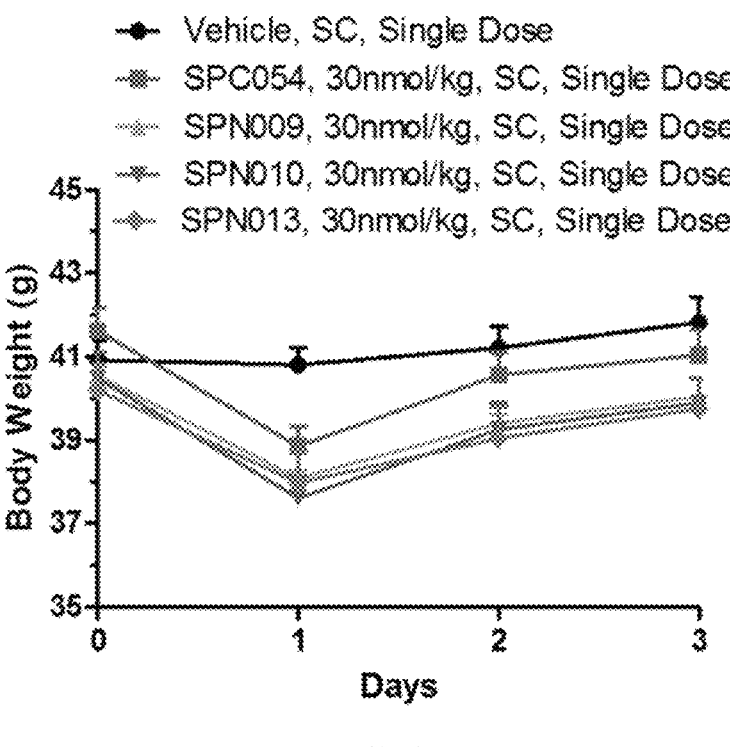
FIG. 3 is a diagram showing the effect of each test drug on the body weight of ob/ob mice in the experiment.
Figure 4:
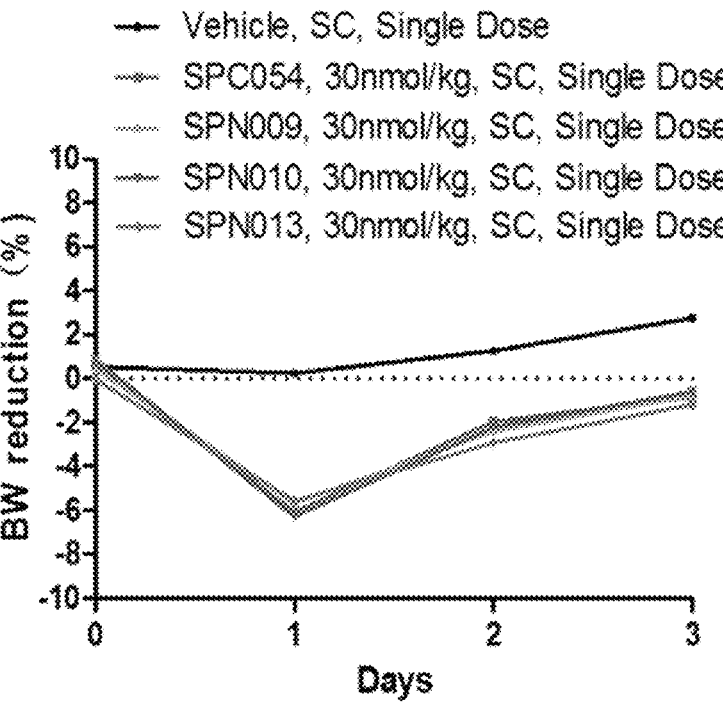
FIG. 4 is a diagram showing the body weight change rate of each test drug to ob/ob mice in the experiment.

As shown in Tables 2 to 4 and FIGS. 1 to 2, the results of blood glucose lowering experiment data and charts showed that when the administration concentration of the polypeptide compound of the disclosure was 30 nmol/kg, the glucose lowering effect was almost consistent with that of Semaglutide; the positive control group and the polypeptide compound group were both significantly different from the solvent control group. As shown in Tables 5-6 and FIGS. 3-4, the solvent control group had no obvious effect on the random weight and the variation of weight of the db/db mice after single subcutaneous injection. The positive control group and the polypeptide compound group were both significantly different from the solvent control group; particularly, the difference was most significant in 24 h following administration. Meanwhile, the experiment results showed that the polypeptide compounds NO: 3, NO: 4 and SPN013 could significantly reduce the random weight variation of the db/db mice in 24 h, 48 h and 72 h following the single subcutaneous injection, which was superior to the Semaglutide group.

Therefore, the single subcutaneous injection of the GLP-1 agonist compound could significantly reduce the random blood glucose of the ob/ob mice with type 2 diabetes, wherein the effects of NO: 3 and NO: 4 were comparable to that of Semaglutide with the same dosage. The NO: 3 and NO: 4 polypeptide compounds showed a better weight control effect.

3. Pharmacokinetic Experiments of Peptide Compounds

Pharmacokinetic comparison experiment of Semaglutide, SPN009 (NO: 3) and SPN010 (NO: 4): 9 male rats, 3 in each group, were respectively given Semaglutide, SPN009 and SPN010. A single subcutaneous injection was performed with a dose of 0.02 mg/kg; blood collection was performed by tail clipping, and the blood collection time points were: 0 h, 15 min, 30 min, 1 h, 2 h, 3 h, 4 h, 6 h, 8 h, 24 h, 48 h and 72 h. The compound concentration in plasma was determined by LC-MS/MS, all data were collected and exported by Unifi 1.9.3 software, and Excel software was used for data calculation. A non-compartmental model of DAS 3.0 software was used to calculate the pharmacokinetic parameters of rats after administration. The results were shown in Table 7.

As shown in Table 7, the main pharmacokinetic parameters $t_{1/2}$ and Tmax of NO: 3 and NO: 4 were comprehensively superior to those of Semaglutide when the rats received a single subcutaneous administration at a concentration of 0.02 mg/kg.

TABLE 2

Effect of each test drug on random blood glucose in db/db mice in experiment (X ± s, n = 8)

| Groups | Dosage(nmol/kg) | Random blood glucose (mmol/L) | Blood glucose at different time after administration (mmol/L) | | | | | | | | |
|---|---|---|---|---|---|---|---|---|---|---|---|
| | | | 0 h | 2 h | 4 h | 6 h | 10 h | 24 h | 36 h | 48 h | 56 h | 72 h |
| Solvent control (PBS) | — | 25.7 ± 3.1 | 29.3 ± 2 | 28.9 ± 3.5 | 29.7 ± 2 | 27.4 ± 2.3 | 33.3 ± 0 | 31.1 ± 2.2 | 30.6 ± 2.2 | 29.3 ± 2.8 | 31.1 ± 2.2 | 33.3 ± 0 |
| Semaglutide | 30 | 25.8 ± 3.9 | 26.8 ± 3.2 | 14.9 ± 4.1 | 13.2 ± 3.2 | 13.3 ± 3.7 | 11.5 ± 3.7 | 12.6 ± 5.6 | 21.1 ± 4.1 | 21.3 ± 5.6 | 28.3 ± 4.8 | 32.3 ± 1.9 |
| NO: 3 | 30 | 25.6 ± 2.7 | 27.3 ± 2 | 15.9 ± 4 | 14.3 ± 3.5 | 14.1 ± 5 | 11.8 ± 3.4 | 11.1 ± 2.4 | 16.7 ± 6.8 | 21 ± 4.1 | 28.9 ± 3.4 | 31.7 ± 1.9 |
| NO: 4 | 30 | 25.5 ± 2 | 26.9 ± 2.7 | 14.4 ± 3.5 | 12.5 ± 2.2 | 13 ± 4.6 | 11.9 ± 4 | 11.1 ± 4.6 | 18.5 ± 8 | 19.6 ± 7.1 | 28 ± 6.1 | 32.5 ± 1.5 |
| SPNO13 | 30 | 25.6 ± 2.7 | 29.6 ± 2 | 15.3 ± 3.3 | 18.2 ± 4.4 | 16.9 ± 4.2 | 17.8 ± 6 | 16 ± 4.5 | 22.7 ± 6.3 | 23.7 ± 3.9 | 31.5 ± 1.5 | 32.4 ± 1.2 |

TABLE 3

Rate of change of random blood sugar of db/db mice with each test drug in experiment

| Groups | Dosage(nmol/kg) | Random blood glucose | Ratio(%) | | | | | | | | | | |
|---|---|---|---|---|---|---|---|---|---|---|---|---|---|
| | | | 0 h | 2 h | 4 h | 6 h | 10 h | 24 h | 36 h | 48 h | 56 h | 72 h |
| Solvent control (PBS) | — | 100.0 | 100.0 | 100.0 | 100.0 | 100.0 | 100.0 | 100.0 | 100.0 | 100.0 | 100.0 | 100.0 |
| Semaglutide | 30 | 100.7 | 91.4 | 51.4 | 44.5 | 48.3 | 34.6 | 40.6 | 68.9 | 72.7 | 91.1 | 96.8 |
| NO: 3 | 30 | 99.6 | 93.0 | 55.1 | 48.3 | 51.4 | 35.5 | 35.7 | 54.5 | 71.7 | 92.9 | 95.1 |
| NO: 4 | 30 | 99.2 | 91.6 | 49.8 | 42.1 | 47.5 | 35.8 | 35.6 | 60.4 | 66.9 | 90.1 | 97.6 |
| SPNO13 | 30 | 99.8 | 100.9 | 53.0 | 61.2 | 61.5 | 53.3 | 51.5 | 74.1 | 81.0 | 101.2 | 97.3 |

TABLE 4

T test of random blood sugar of db/db mice with each test drug in experiment

| Groups | Dosage(nmol/kg) | Random blood glucose | T-Test P value | | | | | | | | | | |
|---|---|---|---|---|---|---|---|---|---|---|---|---|---|
| | | | 0 h | 2 h | 4 h | 6 h | 10 h | 24 h | 36 h | 48 h | 56 h | 72 h |
| Solvent control (PBS) | — | — | — | — | — | — | — | — | — | — | — | — |
| Semaglutide | 30 | 0.92 | 0.08 | 0.00 | 0.00 | 0.00 | 0.00 | 0.00 | 0.00 | 0.00 | 0.16 | 0.14 |
| NO: 3 | 30 | 0.95 | 0.06 | 0.00 | 0.00 | 0.00 | 0.00 | 0.00 | 0.00 | 0.00 | 0.14 | 0.03 |
| NO: 4 | 30 | 0.88 | 0.06 | 0.00 | 0.00 | 0.00 | 0.00 | 0.00 | 0.00 | 0.00 | 0.20 | 0.16 |
| SPNO13 | 30 | 0.97 | 0.80 | 0.00 | 0.00 | 0.00 | 0.00 | 0.00 | 0.00 | 0.01 | 0.70 | 0.05 |

TABLE 5

Random weight of db/db mice with each test drug in experiment (X ± s, n = 8)

| Groups | Dosage (nmol/ kg) | Random body weight at different time after administration (mmol/L) | | | | | |
|---|---|---|---|---|---|---|---|
| | | Day −2 | Day −1 | Day 0 | Day 1 | Day 2 | Day 3 |
| Solvent control (PBS) | — | 40.70 ± 1.40 | 39.64 ± 1.32 | 40.92 ± 1.35 | 40.80 ± 1.19 | 41.21 ± 1.44 | 41.82 ± 1.70 |
| Semaglutide | 30 | 41.37 ± 1.64 | 40.24 ± 1.44 | 41.62 ± 1.56 | 38.86 ± 1.37 | 40.56 ± 1.51 | 41.03 ± 1.72 |
| NO: 3 | 30 | 40.38 ± 0.84 | 39.43 ± 0.83 | 40.55 ± 0.77 | 38.09 ± 0.58 | 39.41 ± 0.57 | 40.06 ± 0.50 |
| NO: 4 | 30 | 40.14 ± 1.62 | 39.21 ± 1.44 | 40.49 ± 1.73 | 37.62 ± 1.48 | 39.26 ± 1.79 | 39.90 ± 1.60 |
| SPNO13 | 30 | 40.22 ± 1.65 | 39.23 ± 1.65 | 40.21 ± 1.65 | 37.98 ± 2.11 | 39.04 ± 2.10 | 39.75 ± 2.13 |

15

TABLE 6

T test of random weight of db/db mice with each test drug in experiment

| Groups | Dosage | T-Test P value | | | | | |
|---|---|---|---|---|---|---|---|
| | | Day −2 | Day −1 | Day 0 | Day 1 | Day 2 | Day 3 |
| Solvent control (PBS) | — | — | — | — | — | — | — |
| Semaglutide | 30 | 0.39 | 0.40 | 0.35 | 0.01 | 0.39 | 0.37 |
| NO: 3 | 30 | 0.58 | 0.71 | 0.51 | 0.00 | 0.01 | 0.01 |
| NO: 4 | 30 | 0.47 | 0.55 | 0.59 | 0.00 | 0.03 | 0.04 |
| SPNO13 | 30 | 0.54 | 0.59 | 0.36 | 0.01 | 0.03 | 0.05 |

TABLE 7

Comparison of pharmacokinetic parameters between Semaglutide and drug candidates

| Parameter | Unit | Semaglutide | | | SPN009 | | | SPN010 | | |
|---|---|---|---|---|---|---|---|---|---|---|
| | | Mean | SD | RSD/% | Mean | SD | RSD/% | Mean | SD | RSD/% |
| AUC(0-t) | µg/L * h | 2244.71 | 293.93 | 13.10 | 2630.55 | 679.80 | 25.80 | 1969.77 | 164.97 | 8.40 |
| AUC(0-∞) | µg/L * h | 2320.02 | 302.12 | 13.00 | 2807.29 | 691.63 | 24.60 | 2064.93 | 123.42 | 6.00 |
| R_AUC(t/∞) | % | 96.77 | 0.09 | 0.90 | 93.53 | 0.18 | 1.90 | 95.30 | 0.26 | 2.70 |
| AUMC(0-t) | h * h * µg/L | 54463.48 | 7571.79 | 13.90 | 73156.82 | 15271.94 | 20.90 | 47513.48 | 2032.32 | 4.30 |
| AUMC(0-∞) | h * h * µg/L | 61264.52 | 9552.95 | 15.60 | 89827.62 | 16348.27 | 18.20 | 56436.94 | 4262.31 | 7.60 |
| t$\frac{1}{2}$z | h | 12.50 | 0.88 | 7.10 | 15.38 | 1.43 | 9.30 | 14.25 | 2.63 | 18.40 |
| Tmax | h | 18.00 | 10.39 | 57.70 | 24.00 | 0.00 | 0.00 | 18.67 | 9.24 | 49.50 |
| Vz/F | L/kg | 0.16 | 0.02 | 14.60 | 0.17 | 0.05 | 29.50 | 0.20 | 0.05 | 24.40 |
| CLz/F | L/h/kg | 0.009 | 0.001 | 11.100 | 0.008 | 0.002 | 25.000 | 0.009 | 0.001 | 11.100 |
| Cmax | µg/L | 58.30 | 7.07 | 12.10 | 66.80 | 16.86 | 25.20 | 47.17 | 5.44 | 11.50 |

What is claimed is:

1. A GLP-1 agonist polypeptide compound, having an amino acid sequence: H Xaa$^1$EGTFTSDVSSYLE Xaa$^2$QAA Xaa$^3$EFIAWLVRGRG (SEQ ID NO: 1), wherein a C-terminal amino acid of the polypeptide compound is a carboxyl or the carboxyl is amidated;

wherein:

Xaa$^1$ is:

Xaa$^2$ is: G,

Xaa$^1$ and Xaa$^2$ are the same or different;

R$_1$ is: a straight-chain or branched-chain alkyl containing 2-6 carbon atoms,

R$_2$ is: H or CH$_3$,

X is: O, S or N—CH$_3$,

R$_1$ is optionally substituted by 1-5 halogen atoms in the case of 2 carbon atoms and 1-6 halogen atoms in the case of 3-6 carbon atoms;

R$_2$ is optionally substituted by 1-3 halogen atoms when R$_2$ is CH$_3$;

Xaa$^3$ is:

n is a natural number ranging from 12 to 20; and m is a natural number ranging from 0 to 3.

2. The GLP-1 agonist polypeptide compound of claim 1, wherein the amino acid sequence of the polypeptide compound is one of the following sequences:

(1)

NO: 1

HX$_2$EGTFTSDVSSYLEX$_2$QAAK(HOOC-(CH$_2$)$_{16}$-CO-$\gamma$-Glu-AEEA-AEEA)EFIAWLVRGRG (2)

NO: 2

HX$_2$EGTFTSDVSSYLEX$_1$QAAK(HOOC-(CH$_2$)$_{16}$-CO-$\gamma$-Glu-AEEA-AEEA)EFIAWLVRGRG (3)

NO: 3

HX$_3$EGTFTSDVSSYLEX$_3$QAAK(HOOC-(CH$_2$)$_{16}$-CO-$\gamma$-Glu-AEEA-AEEA)EFIAWLVRGRG (4)

NO: 4

HX$_3$EGTFTSDVSSYLEX$_1$QAAK(HOOC-(CH$_2$)$_{16}$-CO-$\gamma$-Glu-AEEA-AEEA)EFIAWLVRGRG (5)

NO: 5

HX$_4$EGTFTSDVSSYLEX$_4$QAAK(HOOC-(CH$_2$)$_{16}$-CO-$\gamma$-Glu-AEEA-AEEA)EFIAWLVRGRG (6)

NO: 6

HX$_4$EGTFTSDVSSYLEX$_1$QAAK(HOOC-(CH$_2$)$_{16}$-CO-$\gamma$-Glu-AEEA-AEEA)EFIAWLVRGRG (7)

NO: 7

HX$_5$EGTFTSDVSSYLEX$_5$QAAK(HOOC-(CH$_2$)$_{16}$-CO-$\gamma$-Glu-AEEA-AEEA)EFIAWLVRGRG (8)

NO: 8

HX$_5$EGTFTSDVSSYLEX$_1$QAAK(HOOC-(CH$_2$)$_{16}$-CO-$\gamma$-Glu-AEEA-AEEA)EFIAWLVRGRG (9)

NO: 9

HX$_6$EGTFTSDVSSYLEX$_6$QAAK(HOOC-(CH$_2$)$_{16}$-CO-$\gamma$-Glu-AEEA-AEEA)EFIAWLVRGRG (10)

NO: 10

HX$_6$EGTFTSDVSSYLEX$_1$QAAK(HOOC-(CH$_2$)$_{16}$-CO-$\gamma$-Glu-AEEA-AEEA)EFIAWLVRGRG (11)

NO: 11

HX$_7$EGTFTSDVSSYLEX$_7$QAAK(HOOC-(CH$_2$)$_{16}$-CO-$\gamma$-Glu-AEEA-AEEA)EFIAWLVRGRG (12)

NO: 12

HX$_7$EGTFTSDVSSYLEX$_1$QAAK(HOOC-(CH$_2$)$_{16}$-CO-$\gamma$-Glu-AEEA-AEEA)EFIAWLVRGRG (13)

NO: 13

HX$_8$EGTFTSDVSSYLEX$_8$QAAK(HOOC-(CH$_2$)$_{16}$-CO-$\gamma$-Glu-AEEA-AEEA)EFIAWLVRGRG (14)

NO: 14

HX$_8$EGTFTSDVSSYLEX$_1$QAAK(HOOC-(CH$_2$)$_{16}$-CO-$\gamma$-Glu-AEEA-AEEA)EFIAWLVRGRG (15)

NO: 15

HX$_9$EGTFTSDVSSYLEX$_9$QAAK(HOOC-(CH$_2$)$_{16}$-CO-$\gamma$-Glu-AEEA-AEEA)EFIAWLVRGRG (16)

NO: 16

HX$_9$EGTFTSDVSSYLEX$_1$QAAK(HOOC-(CH$_2$)$_{16}$-CO-$\gamma$-Glu-AEEA-AEEA)EFIAWLVRGRG -continued (17)

NO: 17

HX$_{10}$EGTFTSDVSSYLEX$_{10}$QAAK(HOOC-(CH$_2$)$_{16}$-CO-γ-Glu-
AEEA-AEEA)EFIAWLVRGRG (18)

NO: 18

HX$_{10}$EGTFTSDVSSYLEX$_1$QAAK(HOOC-(CH$_2$)$_{16}$-CO-γ-Glu-AEEA-
AEEA)EFIAWLVRGRG (19)

NO: 19

HX$_{11}$EGTFTSDVSSYLEX$_{11}$QAAK(HOOC-(CH$_2$)$_{16}$-CO-γ-Glu-
AEEA-AEEA)EFIAWLVRGRG (20)

NO: 20

HX$_{11}$EGTFTSDVSSYLEX$_1$QAAK(HOOC-(CH$_2$)$_{16}$-CO-γ-Glu-AEEA-
AEEA)EFIAWLVRGRG (21)

NO: 21

HX$_{12}$EGTFTSDVSSYLEX$_{12}$QAAK(HOOC-(CH$_2$)$_{16}$-CO-γ-Glu-AEEA-
AEEA)EFIAWLVRGRG (22)

NO: 22

HX$_{12}$EGTFTSDVSSYLEX$_1$QAAK(HOOC-(CH$_2$)$_{16}$-CO-γ-Glu-AEEA-
AEEA)EFIAWLVRGRG wherein:

$X_1 = G$; $X_2 = $ $X_3 = $

-continued $X_4 = $ $X_5 = $ $X_6 = $ $X_7 = $ $X_8 = $ $X_9 = $ $X_{10} = $ $X_{11} = $ $X_{12} = $

\* \* \* \* \*

```
                              SEQUENCE LISTING

Sequence total quantity: 1
SEQ ID NO: 1              moltype = AA   length = 31
FEATURE                  Location/Qualifiers
source                   1..31
                         mol_type = protein
                         organism = synthetic construct
SEQUENCE: 1
HXEGTFTSDV SSYLEXQAAX EFIAWLVRGR G                                   31
```